United States Patent [19]

Pearson et al.

[11] Patent Number: 4,731,446

[45] Date of Patent: Mar. 15, 1988

[54] IMIDAZO[1,2-A]PYRIMIDINE SULFONIC ACIDS AND ACID HALIDES

[75] Inventors: Norman R. Pearson, Walnut Creek; William A. Kleschick, Martinez; Shannon L. Bartley, Concord, all of Calif.

[73] Assignee: The Dow Chemical Company, Midland, Mich.

[21] Appl. No.: 45,908

[22] Filed: May 1, 1987

[51] Int. Cl.$^4$ ............................................ C07D 487/14
[52] U.S. Cl. ...................................... 544/281; 71/74; 71/76; 71/77; 71/92; 548/337
[58] Field of Search .......................................... 544/281

[56] References Cited

U.S. PATENT DOCUMENTS

| | | | |
|---|---|---|---|
| 4,349,378 | 9/1982 | Cliff et al. | 71/90 |
| 4,532,243 | 7/1985 | Tully | 544/281 |
| 4,605,433 | 8/1986 | Pearson et al. | 71/90 |
| 4,621,084 | 11/1986 | Takaya et al. | 544/281 |

FOREIGN PATENT DOCUMENTS

| | | | |
|---|---|---|---|
| 0061380 | 9/1982 | European Pat. Off. | 544/281 |
| 951652 | 3/1964 | United Kingdom . | |

OTHER PUBLICATIONS

Ekeley et al., "J. Org. Chem.", vol. 52, 1930, pp. 2026-2028.
Fajgelj et al., *Heterocycles*, No. 24, 1986, pp. 379-386.
Broadbent et al., "J. Chem. Soc., 1965, pp. 3369-3372.

*Primary Examiner*—Glennon H. Hollrah
*Assistant Examiner*—James H. Turnipseed

[57] ABSTRACT

Novel substituted imidazolo[1,2-a]pyrimidine-2-sulfonanilides are prepared from novel substituted imidazolo[1,2-a]pyrimidine-2-sulfonic acids by conversion to the corresponding sulfonyl halides and condensation with substituted anilines and by other methods. N-(2,6-difluorophenyl)-3-chloro-4,6-dimethylimidazolo[1,2-a]pyrimidine-2-sulfonamide is typical of the compounds prepared. The compounds are useful general and selective pre- and post-emergence herbicides.

13 Claims, No Drawings

IMIDAZO[1,2-a]PYRIMIDINE SULFONIC ACIDS AND ACID HALIDES

BACKGROUND OF THE INVENTION

The present invention relates to novel compounds, to herbicidal compositions containing the compounds, to the utility of the compounds for the control of unwanted vegetation, to a process for the manufacture of the compounds, and to certain novel intermediates used in their manufacture.

The control of unwanted vegetation by means of chemical agents, i.e., herbicides, is an important aspect of modern agriculture and land management. While many chemicals that are useful in unwanted vegetation control are known, new compounds that are more effective generally or for specific plant species, are less damaging to desirable vegetation, are safer to man or the environment, are less expensive to use, or have other advantageous attributes are desirable.

It is known that certain 1,2,4-triazolo[1,5-a]pyrimidine-2-sulfonamides possess herbicidal activity (European Application No. 0142152, published May 22, 1985). The compounds are effective against unwanted vegetation when applied to the vegetation or its locus either pre-emergence or post-emergence. Various methods for their preparation and the preparation of the requisite intermediates are also reported. 1,2,4-Triazolo[1,5-a]1,3,5-triazine-2-sulfonamides possessing herbicidal properties are also known (U.S. Pat. No. 4,605,433).

SUMMARY OF THE INVENTION

It has now been found that novel imidazolo[1,2-a]pyrimidine-2-sulfonanilides of the formula

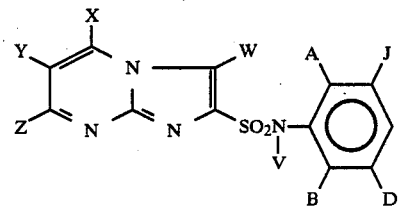

Formula I wherein
- X and Z each, independently represents R, $OR^3$, $SR^3$, $NR^1R^2$, F, Cl, Br, or CN;
- Y represents R, $OR^3$, F, Cl, Br, or CN;
- W represents R, OR, $SO_nR^3$, $NR^1R^2$, F, Cl, Br, $NO_2$, CN, C(O)E, or phenyl, phenoxy, or phenylthio, each phenyl optionally containing 1 to 3 substituents selected from the group consisting of F, Cl, Br, CN, $CF_3$, $NO_2$, and $CH_3$;
- A represents F, Cl, Br, C(O)E, $C_1$-$C_4$ haloalkyl, $NO_2$, CN, $SOR^3$, or $SO_2R^3$;
- B represents F, Cl, Br, CN, R, $OR^3$, $SR^3$, $NR^1R^2$, or phenyl, phenoxy, or phenylthio, each phenyl optionally containing 1 to 3 substituents selected from the group consisting of F, Cl, Br, CN, $CF_3$, $NO_2$, and $CH_3$;
- J and D each, independently represents R, F, Cl, Br, or C(O)E;
- V represents H or $C(O)R^3$;
- R represents H, $C_1$-$C_4$ alkyl or $C_1$-$C_4$ haloalkyl;
- $R^1$ and $R^2$ each, independently represents H or $C_1$-$C_4$ alkyl;
- $R^3$ represents $C_1$-$C_4$ alkyl or $C_1$-$C_4$ haloalkyl;
- E represents R, OR, SR, $NR^1R^2$, or phenyl:
- n represents an integer of 0, 1 or 2;
- and, when V represents H, the agriculturally acceptable salts thereof are useful in the control of unwanted vegetation and can be employed for control of unwanted vegetation in the presence of grassy crops. The compounds of Formula I, usually in the form of herbicidal compositions containing them in addition to an agriculturally acceptable adjuvant or carrier, exhibit herbicidal properties when applied either directly to the unwanted vegetation or to the locus thereof and when applied either pre-emergence or post-emergence.

The present invention encompasses the novel N-benzyl derivatives of the compounds of Formula I, which are useful intermediates in the preparation of herbicidal imidazolo[1,2-a]pyrimidines.

The invention further encompasses a method of preparing the compounds of Formula I and their N-benzyl derivatives by contacting the appropriate corresponding sulfonyl halides with appropriately substituted anilines and a tertiary amine base under conditions conducive to the formation of said compounds. The requisite imidazolo[1,2-a]pyrimidine-2-sulfonyl halide compounds as well as their precursor imidazolo[1,2-a]pyrimidine-2-sulfonic acid compounds and the alkali metal and amine salts thereof are novel and are further manifestations of the present invention.

DETAILED DESCRIPTION OF THE INVENTION

Imidazolo[1,2-a]pyrimidines of Formula I wherein A, B, J, D, W, X, Y, and Z are as defined hereinabove are novel compounds that possess herbicidal properties. While each of the imidazolo[1,2-a]pyrimidine compounds described by Formula I is within the scope of the invention, the degree of herbicidal activity and the spectrum of weed control varies depending upon the substituents present and, consequently, certain of the compounds are preferred. Thus, compounds of Formula I in which X and Z of the pyrimidine ring each, independently represents hydrogen, fluoro, chloro, bromo, $C_1$-$C_4$ alkyl, $C_1$-$C_4$ haloalkyl, $C_1$-$C_4$ alkoxy, or $C_1$-$C_4$ alkylthio are usually preferred. Also in the pyrimidine ring, compounds wherein Y represents hydrogen, chloro, or $C_1$-$C_4$ alkyl are usually preferred. Certain compounds of Formula I possessing electron withdrawing substituents or $C_1$-$C_4$ alkyl in the imidazole ring; that is, compounds in which W represents $C_1$-$C_4$ alkyl, $C_1$-$C_4$ haloalkyl, fluoro, chloro, bromo, nitro, cyano, C(O) $C_1$-$C_4$ alkyl or $CO_2$ $C_1$-$C_4$ alkyl are generally preferred. Compounds of Formula I having at least one electron withdrawing substituent in an ortho position of the aniline ring (substituent A or B) are within the scope of the invention. Those in which A represents fluoro, chloro, bromo, nitro, C(O)E (wherein E is as hereinbefore defined) or $C_1$-$C_4$ haloalkyl are usually preferred. Additionally, those compounds of Formula I wherein B represents fluoro, chloro, bromo, hydrogen, $C_1$-$C_4$ alkyl, $C_1$-$C_4$ haloalkyl, $C_1$-$C_4$ alkoxy, or $C_1$-$C_4$ alkylthio are generally preferred as are those wherein J and D each, independently represents hydrogen or $C_1$-$C_4$ alkyl. Compounds wherein V represents hydrogen and the agriculturally acceptable salts derived therefrom are normally preferred as well.

The term "agriculturally acceptable salts" is employed in this application to denote compounds wherein the acidic sulfonamide proton of the compound of Formula I is replaced by a cation which is not herbicidal, especially to crop plants, nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula $R^5R^6R^7NH^\oplus$ wherein $R^5$, $R^6$, and $R^7$ each, independently represents hydrogen or $C_1-C_{12}$ alkyl, $C_3-C_{12}$ cycloalkyl, or $C_3-C_{12}$ alkenyl, each of which is optionally substituted by one or more hydroxy, $C_1-C_8$ alkoxy, $C_1-C_8$ alkylthio or phenyl groups. Additionally, any two of R5, R6, and $R^7$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

The term "haloalkyl" is employed in this application to describe moieties of the structure $-C_nH(2n+1-m)Q_m$ wherein Q represents F, Cl, or Br and m represents an integer of from 1 to 2n+1. The letter n is an integer of from 1 to 4 for $C_1-C_4$ haloalkyl. Fluorine is a preferred Q and trifluoromethyl is a preferred $C_1-C_4$ haloalkyl moiety. The terms alkyl and haloalkyl relate to both straight chain and branched chain moieties. Thus, typical alkyl groups are methyl, ethyl, 1-methylethyl (isopropyl), 1,1-dimethylethyl (t-butyl), 2-methylpropyl (isobutyl), propyl, and butyl.

The compounds of Formula I wherein V represents hydrogen can generally be prepared by combining an imidazolo[1,2-a]pyrimidine-2-sulfonyl halide of Formula II with an appropriately substituted aniline of Formula III in the presence of a tertiary amine base. The substituents W, X, Y, and Z of Formula II and A, B, J, and D of Formula III are as defined in the Summary of the Invention. The substituent G of Formula II is chloro or bromo.

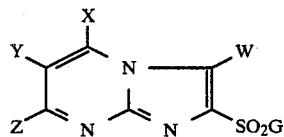
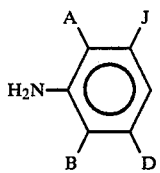

Formula II                Formula III

The preparation is usually accomplished by placing the imidazolo[1,2-a]pyrimidine-2-sulfonyl halide of Formula II, the aniline of Formula III, the tertiary amine base, any solvent employed, and if desired, a nucleophilic catalyst in a flask and heating to effect the reaction. It is sometimes preferred to add the sulfonyl halide to a heated mixture of the other reagents. After a substantial quantity of the compound of Formula I has formed or a substantial quantity of the sulfonyl halide of Formula II has been consumed, the reaction is allowed to cool. The tertiary amine hydrohalide salt by-product sometimes precipitates and can be removed by filtration. Otherwise, any solvent and any excess tertiary amine catalyst are generally removed by evaporation under reduced pressure and the compound of Formula I is recovered by adding excess dilute aqueous base, such as sodium hydroxide or ammonium hydroxide, to the reaction mixture to convert the compound of Formula I to its alkali metal or ammonium salt, which is soluble in the aqueous medium, and to dissolve any residual amine hydrohalide. The resulting solution is typically treated with charcoal and filtered through celite and the filtrate obtained is extracted with a water insoluble solvent, such as ether, and is then acidified with a strong mineral acid, such as hydrochloric acid, to a pH of about 2. The desired compound of Formula I generally precipitates as a solid which is collected and dried.

Approximately equimolar quantities of the compounds of Formulae II and III are generally employed although a substantial excess of one or the other may be employed.

Most tertiary amine bases, such as pyridine, picolines, lutidines, trialkylamines, and aryl dialkylamines are useful in the reaction. Pyridine is preferred. The tertiary amine base can be used in approximately equimolar quantities with the compounds of Formula II or in excess. It is sometimes preferred to use a large excess. If desired, a solvent which is unreactive toward the reagents employed and in which the reagents are soluble can be used. Suitable solvents include acetonitrile, dimethylformamide, toluene, and the like.

The reaction mixture is heated at a sufficiently high temperature and for a sufficient period of time to effect the reaction. Generally, temperatures of about 25° C. to about 150° C. are employed. Temperatures of about 40° C. to about 100° C. are preferred. Times up to about 24 hours are typical and times of from about 1 hour to about 8 hours are preferred. It is preferred to carry out the reaction with stirring and in a flask equipped with means to exclude moisture from the system.

The compounds of Formula I prepared by the above process can be recovered from the reaction mixture as described hereinabove or in other conventional ways such as liquid chromatography, paper chromatography, and crystallization from solvents.

In the same manner compounds of Formula IV, wherein X, Y, Z, W, A, B, D, and J are as defined in the Summary of the Invention, which are N-benzyl derivatives of the compounds of Formula I, can be prepared by the reaction of imidazolo[1,2-a]pyrimidine-2-sulfonyl halides of Formula II with appropriate N-benzylanilines of Formula V.

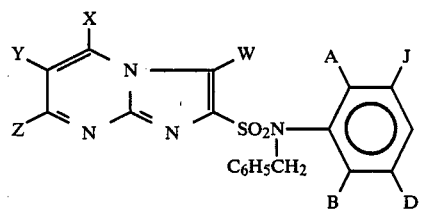

Formula IV

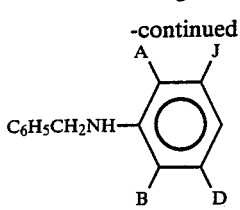

Formula V

The process is carried out in an analogous way except that the product compounds of Formula IV are usually recovered from the reaction mixture by evaporation under reduced pressure to remove the volatile components, extraction with water to remove the by-product amine hydrohalide salts, and recrystallization of the residue from a solvent.

The compounds of Formula IV can additionally be prepared by the reaction of a compound of Formula I wherein V represents hydrogen with benzyl chloride or benzyl bromide. The procedures used are analogous to those employed in the art to benzylate arylsulfonanilides.

The compounds of Formula I wherein V represents hydrogen can further be prepared by condensation of the sulfonyl halides of Formula II with appropriately substituted N-trialkylsilylanilines in the presence of a catalytic amount of an aromatic nitrogen heterocycle (such as pyridine), aliphatic tertiary amine, or dimethyl sulfoxide catalyst. Typically, the compound of Formula II is combined with an equimolar or greater amount of each of the N-trialkylsilylaniline and catalyst in a solvent, such as acetonitrile, under substantially anhydrous conditions and agitated at about 20° to about 90° C. until the reaction is substantially complete.

Compounds of Formula I wherein V represents hydrogen can also be prepared from the analogous compounds of Formula IV by treatment of the latter with aluminum chloride in methylene chloride. Typically, an excess of aluminum chloride is added to a solution of the compound of Formula IV in methylene chloride and the mixture is stirred for several hours at room temperature. The solvent is then removed by evaporation under reduced pressure and an excess of hydrochloric acid is added. The mixture obtained is filtered to collect the crude product of Formula I. This product can be purified by dissolving it in aqueous ammonia and filtering to remove insoluble solids. The filtrate is extracted with a solvent such as ether and then acidified with a dilute mineral acid, such as hydrochloric acid to precipitate the purified product of Formula I, which is collected and dried.

Compounds of Formula I wherein V represents C(O)R$^3$ can be prepared from compounds of Formula I wherein V represents hydrogen by acylation with a compound of the formula R$^3$C(O)Cl using conventional procedures for the acylation of sulfonamides.

Compounds of Formula I wherein X, Y, Z, A, B, J, D, and V are as defined in the Summary of the Invention and W represents SOR$^3$, SO$_2$R$^3$, and C(O)E wherein R$^3$ and E are as defined in the Summary of the Invention can be be prepared from the appropriate corresponding compounds wherein W represents SR$^3$ and CN by applying procedures well known to those skilled in the art for such transformations. Thus, SR$^3$ moieties can be converted to SOR$^3$ and SO$_2$R$^3$ moieties by oxidation with peracetic acid or metachloroperoxybenzoic acid. Cyano groups can be converted to carboxylic acids by acid hydrolysis and the resultant carboxylic acids can be converted to acid chlorides by thionyl chloride. Each of the moieties represented by C(O)E can be prepared by treatment of the acid chloride thus obtained with an appropriate nucleophilic reagent.

Compounds of Formulas I and IV wherein W represents chloro or bromo can readily be prepared by halogenation of a compound of Formula I or IV, respectively, wherein W represents hydrogen. In typical operations, the compound of Formula I or IV wherein W represents hydrogen is combined with an approximately equimolar quantity or an excess of N-chlorosuccinimide or N-bromosuccinimide in a solvent, such as acetonitrile, and the mixture heated to reflux. Additional N-halosuccinimide is added as required to complete the reaction. To recover the product compounds of Formula I, the solvent can be removed by evaporation under reduced pressure and the resulting mixture dissolved in excess dilute aqueous alkali metal base. The solution thus obtained is treated with charcoal, filtered through celite, cooled, and acidified with dilute aqueous mineral acid to a pH of about 2 to precipitate the desired product, which is collected and dried. Suitable bases include sodium hydroxide and suitable acids include hydrochloric acid. To recover the product compounds of Formula IV, the reaction mixture can be extracted with water, concentrated by evaporation under reduced pressure, and the residue recrystallized from an organic solvent.

Certain compounds of Formula IV wherein W represents SR$^3$, F, CN, or phenoxy or phenylthio, each phenyl optionally containing 1 to 3 substituents selected from the group consisting of F, Cl, Br, CN, CF$_3$, NO$_2$, and CH$_3$, with the exception of those wherein one or more of X and Z represents Cl or Br, can be prepared from the corresponding compound of Formula IV wherein W represents chloro or bromo. The conversion is made by contacting an appropriate compound of Formula IV wherein W represents chloro or bromo with a nucleophilic reagent, such as an alkali metal alkylthiolate, haloalkylthiolate, fluoride, cyanide, optionally substituted phenoxide, or optionally substituted phenylthiolate in a suitable solvent and obtaining as intermediates the corresponding compounds of Formula IV wherein W represents SR$^3$, F, CN, or phenoxy or phenylthio, each phenyl optionally containing 1 to 3 substituents selected from the group consisting of F, Cl, Br, CN, CF$_3$, NO$_2$, and CH$_3$. The reaction conditions employed are similar to the conditions used to convert 2-chloropyridine to like derivatives. Thus, the nucleophilic reagent and the 3-chloro or 3-bromoimidazolo[1,2-a]pyrimidine-2-sulfonanilide are combined in a compatible solvent, variously dimethylformamide, dimethyl sulfoxide, butanol, water, toluene, and the like, and heated, if necessary, to effect the reaction. Copper I is sometimes used in place of the alkali metal cation, particularly when cyanide ion is employed as the nucleophilic reagent, and phase transfer catalysts are often employed. The resulting compounds of Formula IV can be recovered by conventional methods.

Compounds of Formulas I and IV wherein W represents NO$_2$ can be prepared by nitration of a compound of Formula I or V, respectively, wherein W represents hydrogen. Conventional techniques for the nitration of nitrogen heterocycles are employed. Compounds of Formulas I and IV wherein W represents amino can be prepared by reduction of the corresponding compounds wherein W represents NO$_2$ and compounds of Formulas I and IV wherein W represents OR or F can be prepared by diazotization of the corresponding compounds wherein W represents amino. Conventional techniques are employed in each of these reactions.

The imidazolo[1,2-a]pyrimidine-2-sulfonyl halides of Formula II can be prepared by treatment of the corresponding imidazolo[1,2-a]pyrimidine-2-sulfonic acids of Formula VI wherein X, Y, Z, and W are as defined in the Summary of the Invention, or their alkali metal or trialkyl ammonium salts with phosphorus oxychloride or oxybromide, optionally in the presence of a poorly nucleophilic tertiary amine base such as N,N-diethylaniline or collidine.

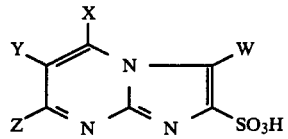

Formula VI

In typical procedures, the compound of Formula VI is combined with an excess of a mixture of approximately equal amounts of phosphorus oxychloride and N,N-diethylaniline and the mixture is heated to about 60–100° C. for 0.2 to 8 hours. The mixture is then allowed to cool and a solvent which is immiscible with water and in which the product is soluble, such as ethyl acetate, methylene chloride, or the like, is added. Water is added cautiously with stirring. The resultant aqueous and organic phases are separated and the organic phase is extracted with dilute aqueous base and evaporated under reduced pressure to obtain the desired compound of Formula VI. Trituration with hexane or ether often facilitates crystallization of the product.

Imidazolo[1,2-a]pyrimidine-2-sulfonic acids of Formula VI and their alkali metal and amine salts can be prepared by condensing an alkali metal or amine salt of 2-aminoimidazole-4-sulfonic acid of Formula VIII, wherein W represents hydrogen, $C_1$–$C_4$ alkyl or $C_1$–$C_4$ haloalkyl, with a 1,3-dicarbonyl compound of Formula VII or a functional equivalent thereof and, if necessary, further modifying the product obtained. The process can be visualized in its simplest form as follows:

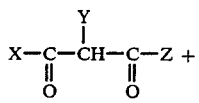

Formula VII

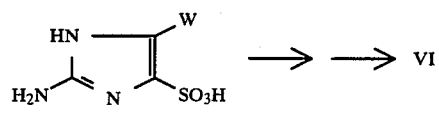

Formula VIII

General methods for a wide variety of condensations of 1,3-dicarbonyl compounds and their functional equivalents with 3-alkylthio-5-amino-1,2,4-triazoles to produce certain 1,2,4-triazolo[1,5-a]pyrimidines, which methods are generally adaptable for the preparation of the imidazolo[1,2-a]pyrimidines of the present invention are disclosed in published European Application 0142152.

In the case of unsymmetrical 1,3-dicarbonyl compounds of Formula VII, two different isomers of the compound of Formula VI can form on condensation. The condensation can be adapted to encourage the formation of either of the possible isomers as is disclosed for the analogous preparation of certain 1,2,4-triazolo[1,5-a]pyrimidines in European Application No. 0142152.

Compounds of Formula VI wherein W, X, Y, and Z each, independently represents hydrogen, $C_1$–$C_4$ alkyl, or $C_1$–$C_4$ haloalkyl can be prepared directly by the condensation of correspondingly substituted 1,3-dicarbonyl compounds of Formula VII with compounds of Formula VIII. The preparation is typically carried out by combining approximately equimolar quanitities of the 1,3-dicarbonyl compound or the acetal or other equivalent of the 1,3-dicarbonyl compound with an alkali metal salt of the compound of Formula VIII in glacial acetic acid and heating until the condensation takes place. Temperatures of about 80° C. to about 120° C. and times of about 0.5 to about 8 hours are typical. The desired acid products or their alkali metal salts generally form as a precipitate in the reaction mixture. The formation of alkali metal salts as the product can be encouraged by removing some of the glacial acetic acid by evaporation under reduced pressure or by using a smaller amount of this solvent in the condensation.

Since either the acids of Formula VIII or their alkali metal salts can be used in the process described for the preparation of compounds of Formula II, the recovery of either of the two or a mixture of the two is satisfactory.

Compounds of Formula VI wherein X and Z represent Cl or Br; Y represents hydrogen, $C_1$–$C_4$ alkyl, $C_1$–$C_4$ haloalkyl, $C_1$–$C_4$ alkoxy, $C_1$–$C_4$ haloalkoxy, or cyano; and W represents hydrogen, $C_1$–$C_4$ alkyl or $C_1$–$C_4$ haloalkyl, can be prepared by condensing compounds of Formula VIII with appropriate 1,3-dicarbonyl compounds of Formula VII wherein X and Z represent $C_1$–$C_4$ alkoxy and Y represents hydrogen, $C_1$–$C_4$ alkyl, or $C_1$–$C_4$ haloalkyl, to obtain intermediates of Formula VI wherein X and Z represent hydroxyl, which intermediates are further treated with phosphoryl chloride or phosphoryl bromide. In a typical preparation, a dialkyl malonate, optionally containing an appropriate substituent in the 2-position, and about two molar equivalents of an alkali metal alcoholate are dissolved in an alcohol and about one molar equivalent of a compound of Formula VIII is added. The resulting solution is heated at about 60° C. to about 120° C. for about 1 to about 10 days. The solid that forms is collected and dissolved in water, and the resulting solution is acidified with dilute mineral acid to obtain intermediates of Formula VI or their alkali metal salts wherein X and Z represent hydroxyl. These are isolated and then combined with an excess of phosphoryl chloride (or bromide) and a solvent, such as acetonitrile, to form a suspension and heated to effect the conversion of the hydroxyl moieties to chloro (or bromo). Temperatures of about 60° C. to about 120° C. and times of about 2 hours to about 24 hours are common. At the higher temperatures and longer times, the corresponding sulfonyl halides of Formula II may form. These can be used directly to prepare compounds of Formula I or can be hydrolyzed to obtain compounds of Formula VI. Compounds of Formula VI can be recovered from the reaction mixture by adding water and a water immiscible solvent, such as methylene chloride, removing the resulting acidic aqueous phase by decantation, and then removing the solvent in the organic phase by evaporation under reduced pressure.

Compounds of Formula VI wherein one of X and Z represents hydrogen, $C_1$-$C_4$ alkyl, or $C_1$-$C_4$ haloalkyl, and the other represents chloro or bromo; Y represents hydrogen, $C_1$-$C_4$ alkyl, $C_1$-$C_4$ haloalkyl, $C_1$-$C_4$ alkoxy, $C_1$-$C_4$ haloalkoxy, fluoro, chloro, bromo, or cyano; and W represents hydrogen, $C_1$-$C_4$ alkyl, or $C_1$-$C_4$ haloalkyl can be prepared by the reaction of appropriate 1,3-dicarbonyl compounds of Formula VII wherein one of X and Z represents hydrogen, $C_1$-$C_4$ alkyl, or $C_1$-$C_4$ haloalkyl, the other represents alkoxy, and Y is defined as above, with appropriate compounds of Formula VIII and subsequently treating the compound obtained with phosphoryl chloride or bromide. In typical operations, the appropriate compound of Formula VII and an approximately equimolar quantity of an appropriate compound of Formula VIII are dissolved in glacial acetic acid and heated to effect a reaction. Temperatures of about 80° C. to about 120° C. and times of about 2 to about 36 hours are typical. The solid product that forms is collected and dried to obtain intermediate compounds of Formula VI wherein one of X and Z represents hydroxyl. These intermediate compounds can be converted to the desired compounds of Formula VI wherein one of X and Z represents chloro or bromo by treating them with excess phosphoryl chloride or bromide in a solvent, as disclosed hereinabove for compounds wherein both X and Z represent chloro or bromo.

Alternatively, compounds of Formula I wherein V represents hydrogen and one or both of X and Z represent chloro or bromo can be prepared from the corresponding compounds of Formula I wherein one or both of X and Z represent hydroxyl by treatment with phosphoryl chloride or bromide. The appropriate compounds of Formula I wherein one or both of X and Z represent hydroxyl can, in turn, be prepared from compounds of Formula I wherein X, Y, and Z each represent hydrogen by treatment with hydrazine in a solvent and heat to obtain the corresponding 2-aminoimidazole-4-sulfonanilide of Formula IX

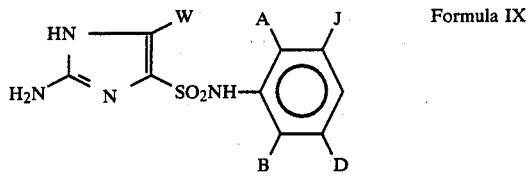

Formula IX wherein A, B, J, D, and W are as defined in the Summary of the Invention as an intermediate. The procedure is analogous to that disclosed in *Heterocycles*, 24 379-386 (1986) for certain other imidazolo[1,2-a]pyrimidines. Alternatively, the compounds of Formula IX can be prepared from the corresponding compounds of Formula I wherein X, Y, and Z each independently represents hydrogen or methyl by adaptation of the method disclosed in application Ser. No. 860,159, filed May 6, 1986, for 3-amino-1,2,4-triazole-5-sulfonanilides. Condensation of the compound of Formula IX with an appropriate 1,3-dicarbonyl compound as defined hereinabove leads to the desired compound of Formula I. The procedures used are generally the same as those described hereinabove for related condensations.

In a similar manner, other compounds of Formula I can be prepared from compounds of Formula I wherein X, Y, and Z each represent hydrogen and W, A, B, D, and J are as defined in the Summary of the Invention by heating the compounds with hydrazine in a solvent to obtain the corresponding 2-aminoimidazole-4-sulfonanilides of Formula IX as intermediates and subsequently condensing these intermediates with a 1,3-dicarbonyl compound or its functional equivalent. The reaction conditions employed are analogous to those used in the related condensations of the compounds of Formula VII with compounds of Formula VIII described hereinabove.

Compounds of Formula VI wherein one or both of X and Z represents $C_1$-$C_4$ alkoxy, $C_1$-$C_4$ haloalkoxy, $C_1$-$C_4$ alkylthio, $C_1$-$C_4$ haloalkylthio, amino, mono- or di-$C_1$-$C_4$ alkylamino, fluoro, or cyano can be prepared from the corresponding compounds of Formula VI wherein one or both of X and Z represents chloro or bromo by treatment with an appropriate nucleophilic reagent, such as an alkali metal $C_1$-$C_4$ alkoxide, $C_1$-$C_4$ haloalkoxide, $C_1$-$C_4$ alkylthiolate, fluoride, or cyanide, or ammonia or a mono- or di-$C_1$-$C_4$ alkylamine. In typical operations, the nucleophilic reagent and compound of Formula VI wherein one or both of X and Z represents chloro or bromo are dissolved in an appropriate solvent and allowed to react. In some cases, heating is required to effect the reaction. Generally, approximately one mole of nucleophilic reagent for each chloro or bromo substituent to be replaced is employed for the anionic nucleophilic reagents and two moles for the amines. The resulting mixture is diluted with water and the desired product is collected by filtration or by removal of the water phase and evaporation of the solvent under reduced pressure.

Compounds of Formula VI wherein X and Z represent hydrogen and Y represents fluoro, chloro, bromo, or $C_1$-$C_4$ alkoxy, can be prepared by the reaction of an N-((3-dimethylamino)-2(halo or $C_1$-$C_4$ alkoxy)-2-propenylidine)-N-methylmethaminium salt with a compound of Formula VIII. The related compounds wherein Y represents methyl can be made in the same way using 3-ethoxymethacrolein as the 1,3-dicarbonyl compound equivalent.

Compounds of Formula VI wherein W represents chloro or bromo can be obtained by chlorination or bromination of the corresponding compounds of Formula VI wherein W represents hydrogen. The reaction conditions employed are analogous to those used in the preparation of compounds of Formula I wherein W represents chloro or bromo from the corresponding compounds of Formula I wherein W represents hydrogen, which conditions are described hereinbefore.

Additional methods for the preparation of the compounds of Formulas I, II, IV, and VI will be apparent to those skilled in the art.

The compounds of Formula VIII can be prepared by appropriate adaptation of the method given in *J. Org. Chem.*, 52, 2026-8 (1930) for the preparation of the compound in which W represents hydrogen.

The anilines of Formula III are known or can be prepared by methods given in published European Application No. 0142152. The N-benzylanilines of Formula V can be prepared from the anilines of Formula III by condensation with benzaldehyde and subsequent reduction using procedures well known to those skilled in the art.

The 1,3-dicarbonyl compounds of Formula VII, N-((3-dimethylamino-2-(halo or $C_1$-$C_4$ alkoxy)-2-propenylidine-N-methylmethaminium salts, and 3- ethoxymethacolein utilized as starting materials are well known in the art.

The following Examples illustrate the preparation of the compounds of this invention and should not be construed as limitations to the claims. The proton nuclear magnetic resonance spectrum of each of the compounds prepared was found to be compatible with the structure assigned.

EXAMPLE 1

Preparation of 4,6-Dimethylimidazolo[1,2-a]pyrimidine-2-sulfonic Acid

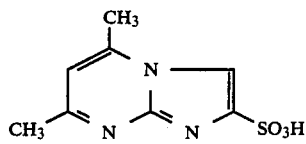

A mixture of 13.1 g (59.1 mmol) of sodium 2-aminoimidazole-4-sulfonate dihydrate, 11.8 g (118 mmol) of 2,4-pentanedione and 150 ml of glacial acetic acid was heated at 100–110° C. for 2 hours. The mixture was then allowed to cool slowly to room temperature and sit overnight. The next day the crystalline solid was collected, washed well with ether and dried to furnish 10.3 gm (77 percent of theory) of the product as a white solid; m.p., more than 300° C.

Analysis:
Calc'd for %C, 42.29; %H, 3.99; %N, 18.48. $C_8H_9N_3O_3S$:
Found: %C, 42.48; %H, 4.00; %N, 18.72.

EXAMPLE 2

Preparation of 4,6-Dimethylimidazolo[1,2-a]pyrimidine-2-sulfonyl Chloride

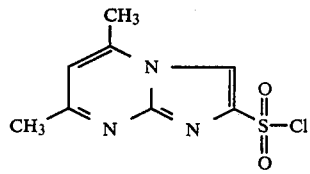

A mixture of 0.60 g (2.6 mmol) of 4,6-dimethylimidazolo[1,2-a]pyrimidine-2-sulfonic acid, 1.2 ml of phosphorus oxychloride and 1.2 ml of N, N-diethylaniline was heated at 75–80° C. for one hour. After cooling to room temperature, the mixture was diluted with 30 ml of ethyl acetate and stirred cautiously with 20 ml of water. The aqueous phase was then separated, neutralized with solid sodium bicarbonate and extracted twice with ethyl acetate. The combined organic extracts were washed twice with saturated aqueous sodium bicarbonate and dried. Evaporation of the solvents gave an oily solid which upon trituration with hexane furnished 0.50 g (78 percent of theory) of the product as a light brown solid; m.p., 178°–179° C. (with decomposition).

Analysis: Calc'd for %C, 39.11; %H, 3.28; %N, 17.10. $C_8H_8ClN_3O_2S$: Found: %C, 39.00; %H, 3.37; %N, 16.98.

EXAMPLE 3

Preparation of N-(2,6-difluorophenyl)-4,6-dimethylimidazolo[1,2-a]pyrimidine-2-sulfonamide (Compound 1)

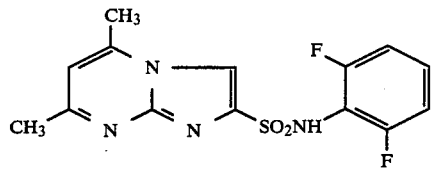

A solution of 1.58 g (12.2 mmol) of 2,6-difluoroaniline in 20 ml of pyridine was treated at room temperature with 3.00 g (12.2 mmol) of 4,6-dimethylimidazolo[1,2-a]pyrimidine-2-sulfonyl chloride and a few crystals of 4-dimethylaminopyridine, and the resulting mixture was stirred at room temperature for two hours, and at 75°–80° C. for one hour. After cooling and allowing to sit overnight, the mixture was filtered and the filtrate concentrated under reduced pressure to an oil which was dissolved in 30 ml of 1.0 N NaOH, stirred with charcoal, and filtered through celite. The filtrate was washed with ether, cooled in ice, and acidified to pH 2 with 3N HCl. The resulting off-white solid product was collected and dried to afford 1.55 g (38 percent of theory) of the title compound; m.p., 272°–273° C.

Analysis: Calc'd for %C, 49.70; %H, 3.58; %N, 16.55 %S, 9.48. $C_{14}H_{12}F_2N_4O_2S$: Found: %C, 49.37; %H, 3.66; %N, 16.55 %S, 9.54.

EXAMPLE 4

Preparation of N-(2,6-difluorophenyl)-3-chloro-4,6-dimethylimidazolo[1,2-a]pyrimidine-2-sulfonamide (Compound 2)

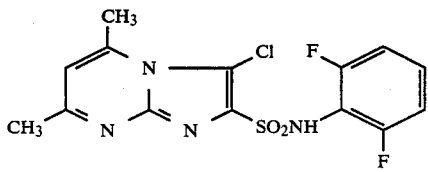

A mixture of 5.00 g (14.8 mmol) of N-(2,6-difluorophenyl)-4,6-dimethylimidazolo[1,2-a]pyrimidine-2-sulfonamide, 2.07 g (15.5 mmol) of N-chlorosuccinimide (NCS) and 100 ml of acetonitrile was heated at reflux (solution occurs) for 2.5 hours. As tlc analysis indicated incomplete reaction, another 0.50 g (3.7 mmol) of NCS was added in several portions over the next 2.5 hours of reflux to complete the reaction. After cooling, concentration of the solution under reduced pressure afforded 7.5 g of an orange solid. This was dissolved in 150 ml of 0.27 N NaOH, and the resulting solution was stirred with charcoal, filtered through celite, cooled in ice and acidified to pH 2 with 3N HCl. The beige solid that formed was collected and dried to afford 4.8 g (87 percent of theory), of the desired product; m.p., dec. above 235° C.

Analysis: Calc'd for %C, 45.11; %H, 2.97; %N, 15.02. $C_{14}H_{11}ClF_2N_4O_2S$: Found: %C, 44.68; %H, 2.87; %N, 15.06.

EXAMPLE 5

Preparation of
N-(2,6-difluorophenyl)-N-benzyl-3-bromo-4,6-dimethylimidazolo-[1,2-a]pyrimidine-2-sulfonamide

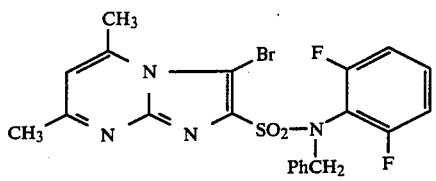

A mixture of 3.70 g (8.64 mmol) of N-(2,6-difluorophenyl)-N-benzyl-4,6-dimethylimidazolo[1,2-a]pyrimidine-2-sulfonamide and 80 ml of acetonitrile was heated to 50° C. (solution occurs) and treated with 1.61 g (9.07 mmol) of N-bromosuccinimide. The resulting solution was stirred at ambient temperature for 3.5 hours and was then diluted with 150 ml of methylene chloride and washed with dilute aqueous sodium bisulfite. The organic phase was dried, concentrated under reduced pressure, and the residue was stirred with ether to afford 4.20 g (96 percent of theory) of the product as a yellow powder; m.p., 156°–158° C.

Analysis: Calc'd for %C, 49.72; %H, 3.38; %N, 11.04. $C_{21}H_{17}BrF_2N_4O_2S$: Found: %C, 49.75; %H, 3.42; %N, 11.01.

EXAMPLE 6

Preparation of
N-(2,6-difluorophenyl)-3-bromo-4,6-dimethylimidazolo[1,2-a]pyrimidine-2-sulfonamide
(Compound 3)

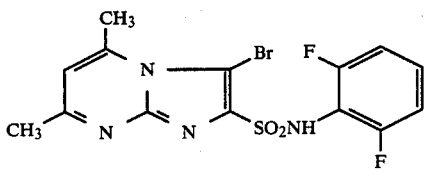

To a solution of 1.50 g (2.96 mmol) of N-(2,6-difluorophenyl)-N-benzyl-3-bromo-4,6-dimethylimidazolo[1,2-a]pyrimidine-2-sulfonamide in 30 ml of methylene chloride was added 1.74 g (13.0 mmol) of aluminum trichloride. The resulting red-orange mixture was stirred at room temperature for 2½ hours and then concentrated under reduced pressure. The residue obtained was stirred with 50 ml of 1.0 N hydrochloric acid for 10 minutes and filtered. The solid obtained was slurried in 100 ml of water, treated with 3.0 ml of concentrated ammonium hydroxide, stirred for 10 minutes and filtered. The filtrate was washed with ether, cooled in ice and acidified to pH 2 with 3 N hydrochloric acid. The white solid that formed was collected, washed with water, and dried to provide 1.10 g (89 percent of theory) of a white powder; m.p., 203°–205° C. (with decomposition).

Analysis: Calc'd for %C, 40.30; %H, 2.66; %N, 13.42. $C_{14}H_{11}BrF_2N_4O_2S$: Found: %C, 40.38; %H, 2.68; %N, 13.42.

EXAMPLE 7

Preparation of
N-(2,6-difluorophenyl)-N-benzyl-3-methylthio-4,6-dimethylimidazolo[1,2-a]pyrimidine-2-sulfonamide

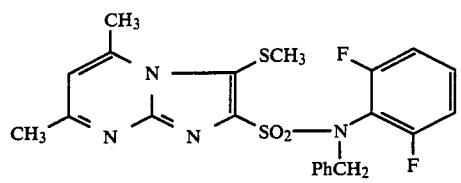

A sample of 0.24 g (5.9 mmol) of sodium hydride (60 percent oil dispersion) was washed three times with hexane, diluted with 30 ml of dimethylformamide (DMF) and treated with 0.29 g (5.9 mmol) of methyl mercaptan. The resulting solution (hydrogen evolution) was stirred at room temperature for 20 minutes and then treated with 2.50 g (5.40 mmol) of N-(2,6-difluorophenyl)-N-benzyl-3-chloro-4,6-dimethylimidazolo[1,2-a]pyrimidine-2-sulfonamide. The solution became dark, exothermed to 37° C. and was stirred for one hour at ambient temperature before adding 0.5 ml of glacial acetic acid and removing the remaining methyl mercaptan to a bleach trap with a stream of nitrogen. After removal of the DMF by evaporation under reduced pressure (xylene chaser), the residue was partitioned between 250 ml of methylene chloride and 75 ml of water. The organic phase was washed with saturated aqueous sodium bicarbonate, dried, and concentrated by evaporation under reduced pressure to obtain a yellow oil. Trituration with ether afforded 2.3 g (90 percent of theory) of the product as a pale, yellow powder; m.p., 191°–194° C.

Analysis: Calc'd for %C, 55.68; %H, 4.25; %N, 11.80. $C_{22}H_{20}F_2N_4O_2S_2$: Found: %C, 55.44; %H, 4.32; %N, 11.58.

EXAMPLE 8

Preparation of
N-(2,6-difluorophenyl)-3-methylthio-4,6-dimethylimidazolo[1,2-a]pyrimidine-2-sulfonamide
(Compound 4)

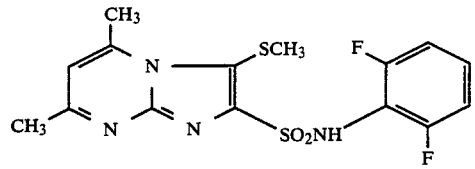

A solution of 1.63 g (3.44 mmol) of N-(2,6-difluorophenyl)-N-benzyl-3-methylthio-4,6-dimethylimidazolo[1,2-a]pyrimidine-2-sulfonamide in 30 ml of methylene chloride was treated with 2.01 g (15.1 mmol) of aluminum trichloride and the resulting red-orange mixture was stirred at room temperature for 3 hours. After removal of the solvent by evaporation under reduced pressure, the residue was stirred with 60 ml of 1.0 N hydrochloric acid for five minutes and filtered. The solid collected was then stirred with 100 ml of water, treated with 3.5 ml of concentrated ammonium hydroxide, and filtered. The filtrate was washed with ether, cooled in ice, and acidified to pH 2 with 3 N hydrochloric acid. The solid that formed was collected, washed with water, and dried under reduced pressure to furnish 1.00 g (76 percent of theory) of the product as a white powder; m.p., 249°–251° C. (with decomposition).

Analysis: Calc'd for %C, 46.87; %H, 3.67; %N, 14.57 %S, 16.68. C$_{15}$H$_{14}$F$_2$N$_4$O$_2$S$_2$: Found: %C, 46.81; %H, 3.76; %N, 14.39 %S, 16.81.

EXAMPLE 9

Preparation of N-(2,6-dichlorophenyl)-4,6-dimethylimidazolo[1,2-a]pyrimidine-2-sulfonamide (Compound 5)

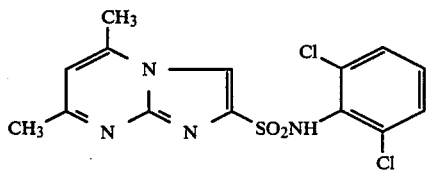

A solution of 1.32 g (8.14 mmol) of 2,6-dichloroaniline and 6.0 ml of pyridine was heated to 73° C. and then treated with 2.00 g (8.14 mmol) of 4,6-dimethylimidazolo[1,2-a]pyrimidine-2-sulfonyl chloride. The resulting mixture was stirred for one hour at ambient temperature and then for 45 minutes at reflux. After cooling and removal of the pyridine by evaporation under reduced pressure, the dark residue was stirred with 10 ml of 2 N sodium hydroxide and 75 ml of water, treated with charcoal, filtered through celite, washed with ether, cooled in ice, and acidified to pH 2 with 3 N hydrochloric acid. The brown powder product was collected and dried under reduced pressure to furnish 0.31 g (10 percent of theory); m.p., 262°–267° C. (with decomposition).

Analysis: Calc'd for %C, 45.30; %H, 3.26; %N, 15.09. C$_{14}$H$_{12}$Cl$_2$N$_4$O$_2$S: Found: %C, 45.04; %H, 3.16; %N, 14.85.

EXAMPLE 10

Preparation of N-benzyl-N-(2,6-difluorophenyl)-4,6-dimethylimidazolo[1,2-a]pyrimidine-2-sulfonamide

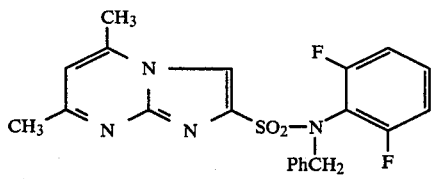

A solution of 1.25 g (5.70 mmol) of N-benzyl-2,6-difluoroaniline in 50 ml of pyridine was treated at room temperature with 1.40 g (5.70 mmol) of 4,6-dimethylimidazolo[1,2-a]pyrimidine-2-sulfonyl chloride and the resulting mixture was stirred at ambient temperature for 40 minutes and at 80°–85° C. for three hours. After removal of the pyridine by evaporation under reduced pressure, the residue was dissolved in 150 ml of methylene chloride, washed with dilute aqueous hydrochloric acid, dried over magnesium sulfate and finally concentrated by evaporation under reduced pressure. The resulting solid was extracted with ether, collected, and dried to provide 1.95 g (80 percent of theory) of the product as a pale yellow powder; m.p., 223°–225° C.

Analysis: Calc'd for %C, 58.87; %H, 4.24; %N, 13.07. C$_{21}$H$_{18}$F$_2$N$_4$O$_2$S: Found: %C, 58.48; %H, 4.22; %N, 12.74.

EXAMPLE 11

Preparation of N-(2,6-difluorophenyl)-N-benzyl-3-cyano-4,6-dimethylimidazolo[1,2-a]pyrimidine-2-sulfonamide

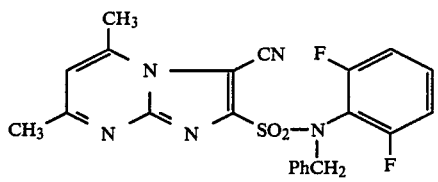

A solution of 9.00 g (17.7 mmol) of N-2,6-difluorophenyl)-N-benzyl-3-bromo-4,6-dimethylimidazolo[1,2-a]pyrimidine-2-sulfonamide in 75 ml of N-methylpyrrolidone (NMP) was treated with 2.86 g (31.9 mmol) of cuprous cyanide and the resulting mixture was heated at 120°–125° C. for two hours. After cooling, the mixture was poured into 250 ml of water and the brown solid that formed was collected. This solid was extracted with 800 ml of methylene chloride and filtered. The filtrate was concentrated by evaporation under reduced pressure to obtain a brown oil. This was charcoaled in hot ethanol-acetonitrile and finally recyrstallized from 10 percent aqueous ethanol to provide 2.40 g (30% of theory) of the product as light brown crystals.

Analysis: Calc'd for %C, 58.27; %H, 3.78; %N, 15.44. C$_{22}$H$_{17}$F$_2$N$_5$O$_2$S: Found: %C, 57.50; %H, 3.94; %N, 14.90.

EXAMPLE 12

Preparation of N-(2,6-difluorophenyl)-3-cyano-4,6-dimethylimidazolo[1,2-a]pyrimidine-2-sulfonamide (Compound 7)

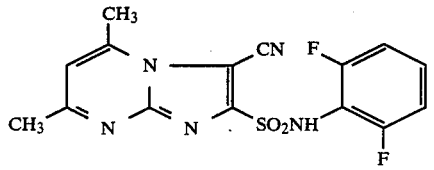

A solution of 2.00 g (4.41 mmol) of N-2,6-difluorophenyl)-N-benzyl-3-cyano-4,6-dimethylimidazolo[1,2-a]pyrimidine-2-sulfonamide and 35 ml of methylene chloride was treated with 2.59 g (19.4 mmol) of aluminum trichloride and the resulting mixture was stirred at room temperature for five hours. After removal of the solvent by evaporation under reduced pressure, the residue was stirred with 75 ml of 1 N hydrochloric acid for five minutes and filtered. The solid obtained was stirred with 4.0 ml of concentrated ammonium hydroxide, diluted with 100 ml of water, and the resulting solution filtered. The filtrate was washed with ether, cooled in ice, and acidified with 3 N hydrochloric acid to pH 2. The white solid that formed was collected, purified by redissolving in aqueous ammonium hydroxide and precipitating with aqueous hydrochloric acid, and finally dried under reduced pressure to yield 1.15 g (72 percent of theory) of the product as a white powder; m.p., 262°–265° C. (with decomposition).

Analysis: Calc'd for %C, 47.25; %H, 3.44; %N, 18.36. $C_{15}H_{11}F_2N_5O_2S\cdot H_2O$: Found: %C, 47.56; %H, 3.09; %N, 18.31.

EXAMPLE 13

Preparation of N-(2,6-difluorophenyl)-N-benzyl-3-chloro-4,6-dimethylimidazolo[1,2-a]pyrimidine-2-sulfonamide

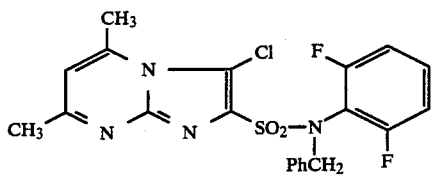

A mixture of 8.50 g (19.8 mmol) of N-2,6-difluorophenyl-N-benzyl-4,6-dimethylimidazolo[1,2-a]pyrimidine-2-sulfonamide and 180 ml of acetonitrile was heated to 50°–55° C. (solution occurs) and treated with 2.78 g (20.8 mmol) of N-chlorosuccinimide (NCS). The resulting mixture (after cooling) was then heated at reflux for three hours, treated with 0.52 g (4.0 mmol) of additional NCS and refluxed another hour. After cooling, a small amount of insoluble material was removed by filtration and the filtrate was diluted with 300 ml of methylene chloride, washed with dilute aqueous sodium bisulfite and then saturated aqueous sodium chloride, dried over magnesium sulfate and concentrated by evaporation under reduced pressure. The solid obtained was recrystallized from 10 percent aqueous ethanol to give 6.3 g (69 percent of theory) of the product as yellow crystals; m.p., 189°–191° C.

Analysis: Calc'd for %C, 54.49; %H, 3.70; %N, 12.10. $C_{21}H_{17}ClF_2N_4O_2S$: Found: %C, 54.28; %H, 3.74; %N, 11.91.

EXAMPLE 14

Preparation of N-(2-trifluoromethylphenyl)-4,6-dimethylimidazolo[1,2-a]pyrimidine-2-sulfonamide (Compound 60)

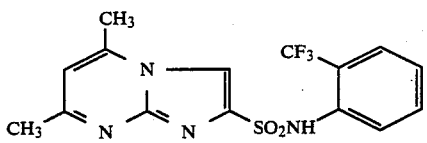

A solution of 3.28 g (20.4 mmol) of 2-aminobenzotrifluoride and 20 ml of pyridine was heated to 48°–50° C. and treated with 5.00 g (20.4 mmol) of 4,6-dimethylimidazolo[1,2-a]pyrimidine-2-sulfonyl chloride. The resulting mixture was then heated at 85°–95° C. for five hours and subsequently concentrated under reduced pressure. The residue was dissolved in 25 ml of 2 N sodium hydroxide and 75 ml of water and the resulting solution was stirred with charcoal, filtered through celite, washed with ether, cooled in ice, and acidified to pH 2 with 3 N hydrochloric acid. The solid that formed was collected and dried to provide 5.60 g (74 percent of theory) of a beige powder; m.p., 213°–215° C.

Analysis: Calc'd for %C, 48.65; %H, 3.54; %N, 15.12. $C_{15}H_{13}F_3N_4O_2S$: Found: %C, 48.37; %H, 3.71; %N, 15.15.

EXAMPLE 15

Preparation of 3-chloro-4,6-dimethylimidazolo[1,2-a]pyrimidine-2-sulfonic acid triethylammonium salt

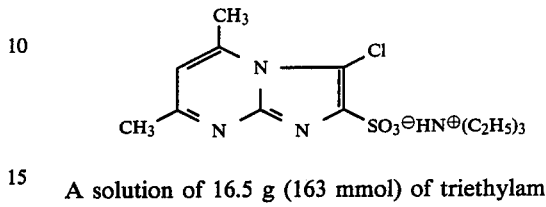

A solution of 16.5 g (163 mmol) of triethylamine in 400 ml of chloroform was treated with 37.0 g (163 mmol) of 4,6-dimethylimidazolo[1,2-a]pyrimidine-2-sulfonic acid. The resulting mixture was heated to boiling and then stirred at ambient temperature for 45 minutes. The reaction mixture was filtered, treated with 23.9 g (179 mmol) of N-chlorosuccinimide, and heated at reflux for three hours. After cooling to room temperature, the solid that formed was collected by filtration, washed with ether, and dried under reduced pressure to provide 45.1 g (76 percent of theory) of the product as a white powder; m.p., >176.5° C. (with decomposition).

Analysis: Calc'd for %C, 46.34; %H, 6.39; %N, 15.44. $C_{14}H_{23}ClN_4O_3S$: Found: %C, 46.31; %H, 6.36; %N, 15.39.

EXAMPLE 16

Preparation of 3-chloro-4,6-dimethylimidazolo[1,2-a]pyrimidine-2-sulfonyl chloride

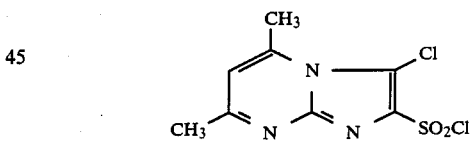

A solution of 15.0 g (41.3 mmol) of triethylammonium 3-chloro-4,6-dimethylimidazolo[1,2-a]pyrimidine-2-sulfonate and 75 ml of phosphorus oxychloride was heated to boiling for 10 minutes and was then quickly cooled to room temperature in an ice bath. The reaction mixture was added dropwise to one liter of water (with vigorous stirring) to hydrolyze the excess phosphorus oxychloride, while maintaining a temperature of 20°–30° C. The solid which formed was collected and dried under reduced pressure to yield 8.83 g (76 percent of theory) of the product as a grey powder; m.p., >159° C. (with decomposition).

Analysis: Calc'd for %C, 34.30; %H, 2.52; %N, 14.99. $C_8H_7Cl_2N_3O_2S$: Found: %C, 33.92; %H, 2.55; %N, 15.03.

EXAMPLE 17

Preparation of N-(2-trifluoromethylphenyl)-3-chloro-4,6-dimethylimidazolo[1,2-a]pyrimidine-2-sulfonamide (Compound 6)

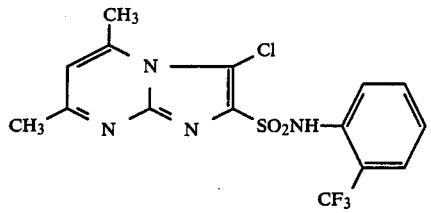

A solution of 1.15 g (7.14 mmol) of 2-aminobenzotrifluoride in 8 ml of pyridine was preheated to 45° C., treated with 2.00 g (7.14 mmol) of 3-chloro-4,6-dimethylimidazolo[1,2-a]pyrimidine-2-sulfonyl chloride and then heated at 85°–95° C. for 1.5 hours with stirring. After cooling to room temperature, the reaction mixture was concentrated by evaporation under reduced pressure and the residue was treated with 40 ml of 0.5 N sodium hydroxide. This mixture was stirred with charcoal, filtered through celite, washed with ether, cooled in ice, and acidified to pH 2 with 3 N hydrochloric acid. The solid that formed was collected and dried under reduced pressure. It was then extracted with boiling acetonitrile and the extract was concentrated by evaporation under reduced pressure. The residue obtained was triturated with ether and dried to yield 1.04 g (36 percent of theory) of the product as a brown powder; m.p., 185°–186° C.

Analysis: Calc'd for %C, 44.51; %H, 2.99; %N, 13.84. $C_{15}H_{12}ClF_3N_4O_2S$: Found: %C, 44.14; %H, 2.91; %N, 14.07.

EXAMPLE 18

Preparation of N-(2-carbomethoxy-6-methylphenyl)-3-chloro-4,6-dimethylimidazolo[1,2-a]pyrimidine-2-sulfonamide (Compound 58)

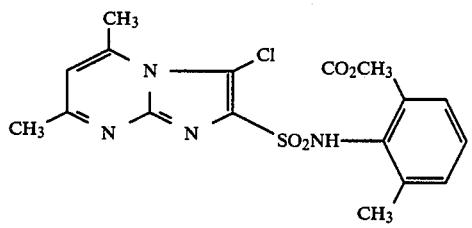

A procedure analogous to that of Example 17 was followed. A yield of 24 percent of theory of the product was obtained; m.p., 194.5°–196° C.

Analysis: Calc'd for %C, 49.96; %H, 4.19; %N, 13.71. $C_{17}H_{17}ClN_4O_4S$: Found: %C, 49.97; %H, 4.27; %N, 13.82.

EXAMPLE 19

Preparation of N-(2,6-dichlorophenyl)-3-chloro-4,6-dimethylimidazolo[1,2-a]pyrimidine-2-sulfonamide (Compound 59)

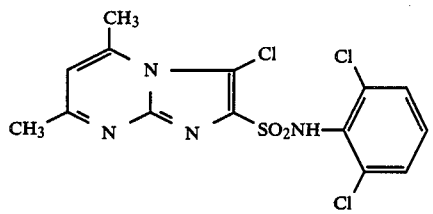

A solution of 12 ml of acetonitrile and 5.86 g (25.0 mmol) of 2,6-dichloro-N-trimethylsilylaniline was treated first with 2.00 g (7.14 mmol) of 3-chloro-4,6-dimethylimidazolo[1,2-a]pyrimidine-2-sulfonyl chloride and then 0.59 ml (8.3 mmol) of dimethyl sulfoxide. The reaction mixture was heated at reflux for 1.5 hours and was then concentrated by evaporation under reduced pressure. The residue obtained was dissolved in 14 ml of 2 N sodium hydroxide and 36 ml of water and the solution obtained was stirred with charcoal, filtered through celite, washed with ether, and acidified to pH 2 with 3 N hydrochloric acid. The resulting solid was collected and dried. It was then extracted with boiling acetonitrile and the extract was concentrated by evaporation under reduced pressure to obtain an oil which was triturated with ether and dried to yield 0.28 g (10 percent of theory) of the product as a tan powder; m.p., >300° C.

Analysis: Calc'd for %C, 41.45; %H, 2.73; %N, 13.81. $C_{14}H_{11}Cl_3N_4O_2S$: Found: %C, 40.75; %H, 2.85; %N, 13.78.

EXAMPLE 20

Preparation of N-(2-chloro-6-methylphenyl)-3-chloro-4,6-dimethylimidazolo[1,2-a]pyrimidine-2-sulfonamide (Compound 57)

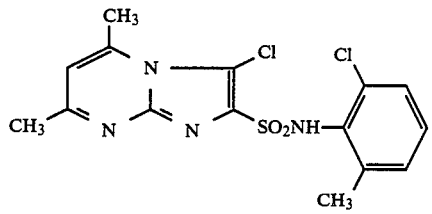

The procedure of Example 19 was followed. The product was obtained as a solid in a yield of 38 percent of theory; m.p., >278° C. (with decomposition).

Analysis: Calc'd for %C, 46.76; %H, 3.66; %N, 14.54. $C_{15}H_{14}Cl_2N_4O_2S$: Found: %C, 46.24; %H, 3.82; %N, 14.95.

EXAMPLE 21

Preparation of sodium 4-hydroxy-6-methylimidazolo[1,2-a]pyrimidine-2-sulfonate, acetic acid salt

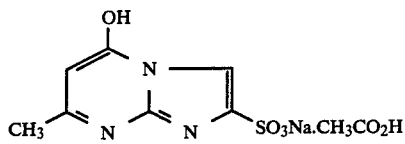

A mixture of 44.1 g (339 mmol) of ethyl acetoacetate, 25.0 g (113 mmol) of sodium 2-aminoimidazole-4-sulfonate dihydrate, and 250 ml of glacial acetic acid was heated at reflux for 42 hours. After cooling, the solid present was collected by filtration, washed with acetic acid and ether, and then dried under reduced pressure to afford 20.3 g (58 percent of theory) of a gray powder; m.p., >250° C.

Analysis: Calc'd for %C, 34.73; %H, 3.24; %N, 13.49. $C_9H_{10}NaN_3O_6S$: Found: %C, 34.50; %H, 3.40; %N, 14.08.

EXAMPLE 22

Preparation of 4-chloro-6-methylimidazolo[1,2-a]pyrimidine-2-sulfonyl chloride

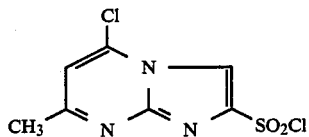

A mixture of 10.0 g (32.1 mmol) of sodium 4-hydroxy-6-methylimidazolo[1,2-a]pyrimidine-2-sulfonate acetic acid salt, 5.1 ml (32.1 mmol) of N,N-diethylaniline, 50 ml of acetonitrile, and 100 ml of phosphorus oxychloride was heated at reflux for 3½ hours. The solvents were then removed by simple distillation under aspirator vacuum with a toluene chaser. The residue obtained was dissolved in 200 ml of methylene chloride, cautiously treated in 100 ml of water and stirred for 20 minutes. The organic phase was separated, washed with water and saturated with aqueous sodium bicarbonate, and dried over magnesium sulfate. Evaporation of the solvent under reduced pressure gave an oil which upon stirring in hexane afforded 6.7 g (78 percent of theory) of a tan powder; m.p., 124°–127° C.

Analysis: Calc'd for %C, 31.60; %H, 1.89; %N, 15.79. $C_7H_5Cl_2N_3O_2S$: Found: %C, 32.80; %H, 2.07; %N, 15.63.

EXAMPLE 23

Preparation of N-(2,6-difluorophenyl)-4-chloro-6-methylimidazolo1,2-a]pyrimidine-2-sulfonamide (Compound 81)

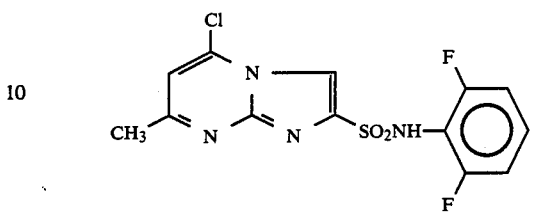

A solution of 5.10 g (19.2 mmol) of 4-chloro-6-methylimidazolo[1,2-a]pyrimidine-2-sulfonyl chloride and 40 ml of dry methylene chloride was cooled to 0°–5° C., treated with 11.6 g (57.5 mmol) of N-trimethylsilyl-2,6-difluoroaniline followed by 3.1 ml (38.4 mmol) of pyridine and was stirred at 0°–5° C. for three hours and then warmed and stirred at room temperature for 16 hours. The resulting mixture was diluted with 200 ml of methylene chloride, washed with dilute aqueous hydrochloric acid and then water, and dried. Evaporation of the solvents under reduced pressure gave a light orange oil which upon trituration with ether furnished a light tan powder. This material was boiled in 200 ml of acetonitrile, allowed to cool, and filtered. The filtrate was concentrated and the residue boiled in about 60 ml of acetonitrile, filtered hot, allowed to cool, filtered again, and the filtrate concentrated to about one third volume and allowed to cool. The crystals that formed were collected, washed with ether, and dried under reduced pressure to provide 2.69 g (39 percent of theory) of product; m.p., 192°–194° C. (dec.).

Analysis: Calc'd for %C, 43.53; %H, 2.53; %N, 15.61. $C_{13}H_9ClF_2N_4O_2S$: Found: %C, 43.53; %H, 2.59; %N, 15.35.

EXAMPLE 24

Preparation of N-(2,6-difluorophenyl)-4-methoxy-6-methylimidazolo[1,2-a]pyrimidine-2-sulfonamide (Compound 45)

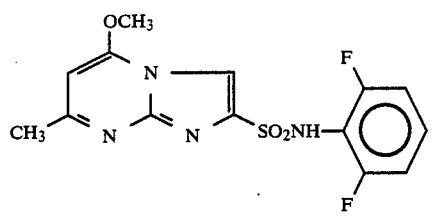

A slurry of 1.25 g (3.48 mmol) of N-(2,6-difluorophenyl)-4-chloro-6-methylimidazolo[1,2-a]-pyrimidine-2-sulfonamide and 15 ml of methanol was cooled to 0°–5° C. and treated dropwise with 1.54 g (7.14 mmol) of 25 weight percent sodium methoxide (in methanol) diluted with 4 ml of methanol. The resulting solution was stirred for 30 minutes at 0°–5° C., treated with 1.0 ml of acetic acid, and then poured into 50 ml of cold water. The white solid formed was collected, washed with water, and dried under reduced pressure to afford 1.20 g (97 percent of theory) of product; m.p., 209°–210° C.

Analysis: Calc'd for %C, 47.46; %H, 3.41; %N, 15.81. $C_{14}H_{12}F_2N_4O_3S$: Found: %C, 46.82; %H, 3.48; %N, 15.19.

EXAMPLE 25

Preparation of N-(2,6-difluorophenyl)-2-formamidoimidazolo-4-sulfonamide

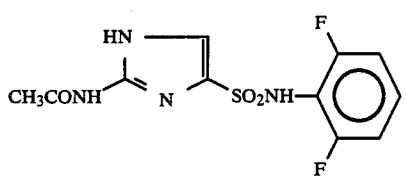

A solution of 0.50 g (1.54 mmoles) of N-(2,6-difluorophenyl)-5-methylimidazolo[1,2-a]pyrimidine-2-sulfonamide in 2.6 ml of 3 M KOH and 3 ml of water was treated dropwise with 1.88 ml (18.5 mmoles) of 30 percent hydrogen peroxide. During the addition, the temperature was maintained below 40° C. by use of a water bath. After stirring for one hour at room temperature, the solution was cooled in ice and acidified with 3 N HCl. The resulting light yellow solid was collected, washed with cold water, and dried under redueed pressure to afford 0.29 g (62 percent of theory) of the product; m.p. >300° C.

Analysis: Calc'd for %C, 39.74; %H, 2.67; %N, 18.54. $C_{10}H_8F_2N_4O_3S$: Found: %C, 38.98; %H, 2.80; %N, 19.13.

EXAMPLE 26

Preparation of N-(2,6-difluorophenyl)-2-aminoimidazolo-4-sulfonamide hydrochloride

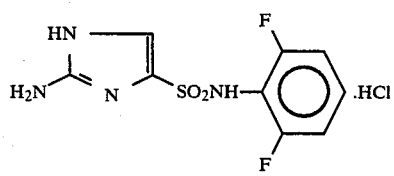

To a mixture of 20 ml of tetrahydrofuran and 14.5 ml of 3 N HCl was added 4.00 g (13.2 mmol) of N-(2,6-difluorophenyl)-2-formamidoimidazolo-4-sulfonamide. The reaction mixture was heated to reflux for one hour and then was allowed to cool to room temperature and sit over the weekend. The solvent was removed under reduced pressure and the residue was triturated with water. The resulting light yellow, crystalline solid was collected and dried to afford 3.63 g (88 percent of theory); m.p., dec. above 234° C.

Analysis: Calc'd for %C, 34.79; %H, 3.02; %N, 18.03. $C_9H_8F_2N_4O_2S \cdot HCl$: Found: %C, 34.62; %H, 2.99; %N, 17.99.

EXAMPLE 27

Preparation of N-(2,6-difluorophenyl)-4,6-bishydroxyimidazolo[1,2-a]pyrimidine-2-sulfonamide monohydrate

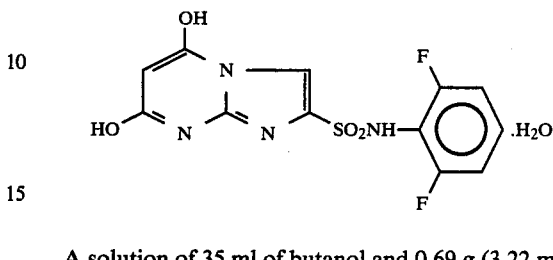

A solution of 35 ml of butanol and 0.69 g (3.22 mmol) of sodium methoxide in methanol (25 percent by weight) was distilled to the constant boiling point of butanol. The solution was allowed to cool to room temperature and was treated with 0.20 g (0.64 mmol) of N-(2,6-difluorophenyl)-2-aminoimidazolo-4-sulfonamide, hydrochloride, followed by 0.206 g (1.29 mmol) of diethyl malonate. The reaction mixture was heated to reflux for 42 hours, cooled slightly, then concentrated under reduced pressure. The residue was triturated with water, washed twice with 25 ml ether, chilled, and acidified to pH2 with 3 N HCl. The tan solid that formed was collected, washed with water, and dried to afford 0.07 g (32 percent of theory) of the product; mp., dec. above 198° C.

Analysis: Calc'd for %C, 40.01; %H, 2.78; %N, 15.55. $C_{12}H_8F_2N_4O_4S \cdot H_2O$: Found: %C, 39.89; %H, 2.93; %N, 15.69.

EXAMPLE 28

Preparation of N-(2,6-difluorophenyl)-4,6-dichloroimidazolo[1,2-a]pyrimidine-2-sulfonamide (Compound 91)

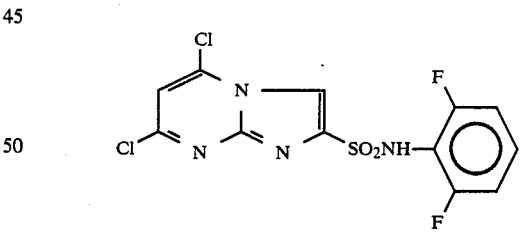

A mixture of 6.30 g (17.5 mmol) of N-(2,6-difluorophenyl)-4,6-bishydroxyimidazolo[1,2-a]pyrimidine-2-sulfonamide, monohydrate in 50 ml of phosphorus oxychloride was heated to reflux for two hours then allowed to cool. The excess solvent was was distilled under reduced pressure. The residue as stirred with 10 ml of toluene then distilled to remove the solvent. The residue was triturated with ether to afford a brown solid which was collected, washed well with water and dried to yield 4.9 g (73 percent of theory) of the product. This compound is unstable; the structure assignment is based on proton NMR spectral data.

EXAMPLE 29

Preparation of N-(2,6-difluorophenyl)-4,6-bismethoxyimidazolo1,2-a]-pyrimidine-2-sulfonamide monohydrate (Compound 89)

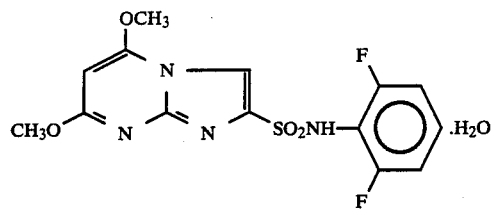

A mixture of 0.80 g (2.11 mmol) of N-(2,6-difluorophenyl)-4,6-dichloroimidazolo[1,2-a]pyrimidine-2-sulfonamide in 6 ml of methanol was treated with 1.46 g (6.75 mmol) of sodium methoxide (25 percent by weight in methanol). After stirring for 30 minutes at room temperature, the solvent was removed under reduced pressure and the residue neutralized with acetic acid. Trituration with water gave a tan solid which was extracted with boiling methanol, collected and dried under reduced pressure to afford 0.59 g (72 percent of theory); m.p., 200°–202° C.

Analysis: Calc'd for %C, 43.30; %H, 3.63; %N, 14.43. $C_{14}H_{12}F_2N_4O_4S \cdot H_2O$: Found: %C, 43.75; %H, 3.28; %N, 14.19.

Additional compounds of the invention that can be prepared by the methods provided and in the art available to the skilled chemist include the imidazolo[1,2-a]pyrimidine-2-sulfonic acid (Formula V) and -sulfonyl halide (Formula II) examples of Table I and the imidazolo[1,2-a]pyrimidine-2-sulfonanilide examples of Table II. The following compounds of Table II were found to have the correct NMR spectra and elemental (CHN) analyses and to have the following melting points: Compound 69, >300° C.; 70, >300° C.; 72, 264°–6° C. (dec); 73, 222°–6° C.; (dec); 75, 196°–7.5° C.; 76, 264° C. (dec); 77, 190.5°–2.5° C.; 78, >284° C. (dec); 45, 209°–10° C.; 46, 204°–6° C.; 50, 192°–4° C. (dec); and 90, 212° C. (dec).

TABLE I

IMIDAZOLO[1,2-a]PYRIMIDINE-2-SULFONIC ACIDS AND SULFONYL HALIDES
(Substituents Refer to Formulae II and VI)

| X | Y | Z | W | G or OH |
|---|---|---|---|---------|
| $OCH_3$ | H | $CH_3$ | Cl | OH |
| $OC_2H_5$ | H | $CH_3$ | 2-Cl—4-$CF_3$—phenoxy | Cl |
| $CF_3$ | H | $CH_3$ | H | OH |
| $CF_3$ | H | $CH_3$ | $CH_3$ | Cl |
| $OCH_3$ | H | $OCH_3$ | F | OH |
| $OCH_3$ | H | $OCH_3$ | $OCH_3$ | Br |
| H | H | $CH_3$ | $CF_3$ | OH |
| H | H | $CH_3$ | Br | OH |
| H | H | $CH_3$ | H | Cl |
| n-$C_4H_9$ | H | $CH_3$ | $NO_2$ | OH |
| $SCH_3$ | H | $CH_3$ | $SCH_3$ | OH |
| $SCH_3$ | H | $CH_3$ | $CH_3$ | Cl |
| $OCF_2CCl_2H$ | H | $CH(CH_3)C_2H_5$ | $CO_2C_4H_9$ | Cl |
| $OC_4H_9$ | H | $C_4F_9$ | $COCH_3$ | Cl |
| CN | H | $N(CH_3)_2$ | CN | Cl |
| $SCCl_3$ | H | $SCCl_3$ | $SCCl_3$ | OH |
| $OCF_3$ | H | $NHC_4H_9$ | $NHC_4H_9$ | Br |
| Cl | Cl | Cl | $C_6H_5$ | Cl |
| Br | Cl | Br | $COCF_3$ | OH |
| H | H | H | $SO_2CF_3$ | OH |
| H | $C(CH_2Br)_3$ | $NH_2$ | $SOC_4H_9$ | OH |
| H | $OCH_3$ | H | 3,5-di$CH_3$—4-$NO_2$—phenoxy | OH |
| H | $O(CH_2)_4Cl$ | H | 4-CN—3-F—5-$CH_3$—phenylthio | OH |
| $CH_3$ | Br | H | $OCF_2CF_2H$ | Br |
| $CF_3$ | $OCH_2CH(CH_3)_2$ | $CF_3$ | $CON(CH_3)_2$ | Cl |
| F | H | $C(CH_3)_3$ | F | OH |
| $NHCH_3$ | CN | $NHCH_3$ | $C_3F_7$ | OH |
| $N(C_4H_9)_2$ | F | CN | H | Cl |
| F | $OCF_3$ | F | $COC_6H_5$ | Cl |
| Cl | $CH_3$ | Cl | Cl | OH |
| Br | n-$C_4H_9$ | H | OH | Br |
| H | Cl | H | F | OH |
| $NH_2$ | Cl | H | $CONH_2$ | OH |
| Cl | H | $CH_3$ | H | Cl |

TABLE II

IMIDAZOLO[1,2-a]PYRIMIDINE-2-SULFONAMIDE COMPOUNDS
(Substituents Refer to Formula I)

| Compound Number | X | Y | Z | W | A | B | J | D |
|---|---|---|---|---|---|---|---|---|
| 6 | $CH_3$ | H | $CH_3$ | Cl | $CF_3$ | H | H | H |
| 7 | $CH_3$ | H | $CH_3$ | CN | F | F | H | H |
| 8 | $OC_2H_5$ | H | $CH_3$ | Cl | Cl | Cl | H | H |
| 9 | $OC_2H_5$ | H | $CH_3$ | $CF_3$ | $CF_3$ | $OCH_3$ | H | H |

TABLE II-continued
IMIDAZOLO[1,2-a]PYRIMIDINE-2-SULFONAMIDE COMPOUNDS
(Substituents Refer to Formula I)

| Compound Number | X | Y | Z | W | A | B | J | D |
|---|---|---|---|---|---|---|---|---|
| 10 | $OC_2H_5$ | H | $CH_3$ | F | $NO_2$ | $CH_3$ | H | H |
| 11 | $OC_2H_5$ | H | $CH_3$ | $CH_3$ | F | F | $CH_3$ | H |
| 12 | $CF_3$ | H | $CH_3$ | H | $CF_3$ | $SCH_3$ | H | H |
| 13 | $CF_3$ | H | $CH_3$ | Cl | F | H | H | H |
| 14 | $CF_3$ | H | $CH_3$ | F | Cl | Cl | $CH_3$ | H |
| 15 | H | H | $CH_3$ | Cl | $CF_3$ | $OCH_3$ | H | H |
| 16 | H | H | $CH_3$ | F | Cl | Cl | H | H |
| 17 | H | H | $CH_3$ | CN | Cl | Cl | $CH_3$ | H |
| 18 | H | Cl | H | Cl | $CF_3$ | $SCH_3$ | H | H |
| 19 | H | Cl | H | F | Br | Cl | H | H |
| 20 | $OCH_3$ | H | $OCH_3$ | Cl | $CF_3$ | H | H | H |
| 21 | $OCH_3$ | H | $OCH_3$ | F | $CO_2CH_3$ | Cl | H | Cl |
| 22 | $OCH_3$ | H | $OCH_3$ | $OCH_3$ | Cl | Cl | $CH_3$ | H |
| 23 | $n-C_4H_9$ | H | $CF_3$ | $SO_2CH_2Cl$ | $CF_3$ | $CH_3$ | Cl | Cl |
| 24 | $C_4F_9$ | H | $C_4F_9$ | $OCF_2CCl_2H$ | Cl | $C(CH_3)_3$ | Cl | H |
| 25 | $OC_4H_9$ | H | $CH(CH_3)C_2H_5$ | $OC_4H_9$ | $CON(CH_3)_2$ | Br | $CH_3$ | $CH_3$ |
| 26 | CN | H | $SC_3H_7$ | $SC_3H_7$ | $CO_2C_4H_9$ | $CO_2C_4H_9$ | F | H |
| 27 | $OCF_2CBr_2H$ | H | $OCF_2CBr_2H$ | H | $CONH_2$ | $CF_3$ | H | F |
| 28 | $SCH_3$ | $CH_3$ | $CH_3$ | $CO_2C_4H_9$ | $COSC_4H_9$ | $CHCl_2$ | $CHCl_2$ | Cl |
| 29 | $NHCH_3$ | $C_4H_9$ | $NHCH_3$ | $C_6H_5$ | $CO_2H$ | $C_6H_5$ | H | Br |
| 30 | $SCH_2CH(CH_3)_2$ | F | $N(C_4H_9)_2$ | $COCF_3$ | $COC_6H_5$ | $NHC_4H_9$ | H | H |
| 31 | F | H | $C(CH_3)_3$ | COH | $(CH_2)_4Cl$ | H | H | $(CH_2)_4Cl$ |
| 32 | Cl | Cl | Cl | 2-Br—6-F—4-$CH_3$—phenoxy | $NO_2$ | $OCF_3$ | Br | $CH_3$ |
| 33 | Cl | Cl | H | 4-$CF_3$ phenylthio | CN | CN | $C(CH_3)_3$ | H |
| 34 | $N(CH_3)_2$ | $OC_2H_5$ | $CH_3$ | 2-CN—4-$NO_2$ phenyl | $SO_2CF_3$ | $CF_2CHFC_2F_5$ | H | H |
| 35 | CN | CN | $OCH(CH_3)_2$ | $C_4F_9$ | $SO_2C_4F_9$ | $OC_4H_9$ | H | H |
| 36 | F | $C_2F_5$ | F | $N(CH_3)_2$ | Cl | $NO_2$ | H | $n-C_4H_9$ |
| 37 | H | $OCF_3$ | Br | $NHC_4H_9$ | $CF_3$ | $CO_2N(CH_3)_2$ | H | $CF_3$ |
| 38 | $CH_3$ | $CCl_3$ | CN | $NO_2$ | Cl | $SO_2C_4H_9$ | $C_4H_9$ | H |
| 39 | $OC_4H_9$ | F | F | $COSC_4H_9$ | Cl | 2,6-diF—4-$CH_3$ phenyl | H | H |
| 40 | Br | H | Br | $COC_6H_5$ | Br | 2-Cl—4-$NO_2$ phenoxy | Br | H |
| 41 | Cl | H | Cl | Br | $CF_3$ | H | H | H |
| 42 | H | Cl | H | $COC_4H_9$ | $CF_3$ | $SOC_3H_7$ | H | H |
| 43 | H | H | H | Cl | $CF_3$ | H | H | H |
| 44 | $CH_3$ | $CH_3$ | $CH_3$ | F | CN | 4-CN phenylthio | $CH_3$ | $CH_3$ |
| 45 | $OCH_3$ | H | $CH_3$ | H | F | F | H | H |
| 46 | $OCH_3$ | H | $CH_3$ | Br | F | F | H | H |
| 47 | $OCH_3$ | H | $CH_3$ | CN | $CO_2CH_3$ | $CH_3$ | H | H |
| 48 | $SCH_3$ | H | $CH_3$ | F | $CF_3$ | $OC_2H_5$ | H | H |
| 49 | $SCH_3$ | H | $CH_3$ | Cl | Cl | $CH_3$ | H | H |
| 50 | Cl | H | $CH_3$ | H | F | F | H | H |
| 51 | $OC_2H_5$ | H | $CH_3$ | CN | $CO_2C_4H_9$ | $CH_3$ | H | H |
| 52 | $OC_2H_5$ | H | $CH_3$ | $NO_2$ | $CF_3$ | $OCH_2CF_3$ | H | H |
| 53 | $OC_2H_5$ | H | $CH_3$ | H | $CF_3$ | H | H | H |
| 54 | $OC_2H_5$ | H | $CH_3$ | Br | Br | $CH_3$ | H | H |
| 55 | $OC_2H_5$ | H | $CH_3$ | $NH_2$ | F | F | H | H |
| 56 | $OC_2H_5$ | H | $CH_3$ | H | Cl | Cl | H | H |
| 57 | $CH_3$ | H | $CH_3$ | Cl | Cl | $CH_3$ | H | H |
| 58 | $CH_3$ | H | $CH_3$ | Cl | $CO_2CH_3$ | $CH_3$ | H | H |
| 59 | $CH_3$ | H | $CH_3$ | Cl | Cl | Cl | H | H |
| 60 | $CH_3$ | H | $CH_3$ | H | $CF_3$ | H | H | H |
| 61 | $CH_3$ | H | $CH_3$ | F | F | F | H | H |
| 62 | $CH_3$ | H | $CH_3$ | $CO_2CH_3$ | F | F | H | H |
| 63 | $CH_3$ | H | $CH_3$ | $CF_3$ | F | F | H | H |
| 64 | $CH_3$ | H | $CH_3$ | $NO_2$ | F | F | H | H |
| 65 | $CH_3$ | H | $CH_3$ | $CONH_2$ | F | F | H | H |
| 66 | $CH_3$ | H | $CH_3$ | $OCH_3$ | F | F | H | H |
| 67 | $CH_3$ | H | $CH_3$ | Cl | $NO_2$ | $CH_3$ | H | H |
| 68 | $CH_3$ | H | $CH_3$ | Cl | $CF_3$ | $OCH_3$ | H | H |
| 69 | $CH_3$ | H | $CH_3$ | Cl | Cl | Cl | $CH_3$ | H |
| 70 | $CH_3$ | H | H | Cl | F | F | H | H |
| 71 | $CH_3$ | H | H | CN | F | F | H | H |
| 72 | $CH_3$ | H | H | H | F | F | H | H |
| 73 | H | H | $CH_3$ | H | F | F | H | H |
| 74 | H | H | $CH_3$ | Cl | F | F | H | H |
| 75 | H | $CH_3$ | H | H | $CF_3$ | H | H | H |
| 76 | H | $CH_3$ | H | Cl | F | F | H | H |
| 77 | H | $CH_3$ | H | Cl | $CF_3$ | H | H | H |
| 78 | H | $CH_3$ | H | H | F | F | H | H |
| 79 | H | $CH_3$ | H | Br | F | F | H | H |
| 80 | H | $CH_3$ | H | $SO_2CH_3$ | F | F | H | H |
| 81 | Cl | H | $CH_3$ | H | F | F | H | H |

TABLE II-continued
IMIDAZOLO[1,2-a]PYRIMIDINE-2-SULFONAMIDE COMPOUNDS
(Substituents Refer to Formula I)

| Compound Number | X | Y | Z | W | A | B | J | D |
|---|---|---|---|---|---|---|---|---|
| 82 | CH$_3$ | H | OCH$_3$ | Cl | F | F | H | H |
| 83 | CH$_3$ | H | Cl | Br | F | F | H | H |
| 84 | CH$_3$ | H | CF$_3$ | H | CF$_3$ | H | H | H |
| 85 | CF$_3$ | H | CH$_3$ | H | CF$_3$ | H | H | H |
| 86 | OCH$_3$ | H | Cl | H | CF$_3$ | H | H | H |
| 87 | CF$_3$ | H | CH$_3$ | H | F | F | H | H |
| 88 | CF$_3$ | H | CH$_3$ | Cl | F | F | H | H |
| 89 | OCH$_3$ | H | OCH$_3$ | H | F | F | H | H |
| 90 | OCH$_3$ | H | OCH$_3$ | Br | F | F | H | H |

While it is possible to utilize the imidazolo[1,2-a]pyrimidine-2-sulfonanilide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-C$_{18}$ ethoxylate; alcohol-alkylene oxide addition products, such as tridecyl alcohol-C$_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters and sprayers, by addition to irrigation water, and by other conventional means known to those skilled in the art.

The compounds of Formula I have been found to be useful preemergence and postemergence herbicides. Some of the compounds are useful for the selective control of broadleaf plants in grass crops, such as corn, wheat, barley, and rice and are especially useful in the selective control of broadleaf weeds in wheat. Examples of the types of broadleaf weeds controlled include various species of prickly sida, morning glory, cocklebur, jimsonweed, velvet leaf, pigweed and black nightshade. Certain grassy weeds, such as crabgrass and yellow foxtail are also controlled. As will be appreciated by those skilled in the art, not all of the compounds control all of the weeds or are selective for all of the crops.

The term "herbicide" is used herein to mean an active ingredient which controls or adversely modifies growth of plants. By "growth controlling" or "herbicidally effective" amount is meant an amount of active ingredient which causes an adversely modifying effect and includes deviations from natural development, killing, regulation, dessication, retardation, and the like. The terms "plants" and "weeds" are meant to include germinant seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of the test, the specific compound employed, the specific adjuvants and carriers employed, and the like, as well as the amount of chemical applied. These and other factors can be adjusted as is known in the art to promote selective herbicidal action. Generally, it is preferred to apply the compounds of Formula I post-emergence to relatively immature plants to achieve the maximum control of broadleaf weeds. It is more preferred to employ the compounds under circumstances where broadleaf weeds are controlled in the presence of wheat.

Application rates of about 0.001 to about 20 Kg/Ha are generally employed in post-emergence operations; for pre-emergence applications, rates of about 0.01 to about 20 Kg/Ha are generally employed.

The following utility examples are illustrative of the herbicidal activity exhibited by compounds of Formula I.

EXAMPLE 30

Evaluation of Post-Emergence Herbicidal Activity

Representative compounds of Formula I were evaluated for the post-emergence control of a variety of species of plants. In these evaluations the test plants were grown to a height of about 4 inches and were then sprayed to run-off with aqueous compositions containing known concentrations of the compounds using conventional spray equipment. The spray compositions were prepared by mixing the required amount of active ingredient and an emulsifier or dispersant in an aqueous acetone carrier to form an emulsion or suspension. Control plants were sprayed in the same manner with like compositions omitting the active ingredient. Thereafter, the plants were maintained in a greenhouse under conditions conducive to plant growth. Two weeks after treatment the plants were examined for growth and evaluated on a scale of 0 to 100 where 0 represents no effect and 100 represents complete kill. In this test 100 ppm represents about 0.25 Kg/Ha. The compounds and plant species tested, the application rates employed, and the results obtained in this test are given in Table III.

TABLE III

| | | POST-EMERGENCE HERBICIDAL ACTIVITY | | | | | | | |
|---|---|---|---|---|---|---|---|---|---|
| Compound Number | Rate, ppm | Cocklebur | Jimsonweed | Morning Glory | Pigweed | Velvet Leaf | Corn | Rice | Wheat |
| 1 | 2000 | 0 | 50 | 20 | 40 | 30 | 0 | 0 | 0 |
| 2 | 2000 | 90 | 90 | 90 | 100 | 98 | 95 | 90 | 45 |
|   | 125  | 50 | 90 | 70 | 95 | 98 | 65 | 65 | 20 |
| 3 | 2000 | 75 | 100 | 70 | 100 | 98 | 85 | 70 | 30 |
|   | 125  | 60 | 50 | 80 | 90 | 60 | 50 | 20 | 0 |
| 4 | 2000 | 0 | 30 | 50 | 95 | 40 | 20 | 0 | 0 |
| 5 | 2000 | 20 | 0 | 30 | 75 | 40 | 0 | 0 | 0 |
| 6 | 2000 | 90 | 50 | 95 | 100 | 100 | 25 | 90 | 40 |
|   | 125  | 75 | 0 | 95 | 60 | 95 | 0 | 40 | 0 |
| 7 | 2000 | 98 | 100 | 100 | 100 | 100 | 0 | 0 | 0 |
|   | 125  | 50 | 60 | 80 | 0 | 98 | 0 | 0 | 0 |
| 45 | 2000 | 0 | 30 | 40 | 15 | 20 | 5 | 0 | 0 |
| 46 | 2000 | 70 | 80 | 60 | 100 | 90 | 60 | 20 | 20 |
|    | 125  | 0 | 60 | 50 | 100 | 60 | 60 | 0 | 15 |
| 57 | 2000 | 30 | 35 | 30 | 20 | 50 | 0 | 0 | 0 |
| 58 | 2000 | 35 | 60 | 70 | 0 | 75 | 0 | 0 | 0 |
| 59 | 2000 | 50 | 60 | 75 | 100 | 80 | 0 | 60 | 0 |
| 69 | 2000 | 40 | 40 | 60 | 30 | 40 | 0 | 0 | 0 |
| 70 | 2000 | 35 | 40 | 0 | 50 | 60 | 0 | 0 | 0 |
| 72 | 2000 | 0 | 0 | 0 | 30 | 60 | 0 | 25 | 0 |
| 76 | 2000 | 70 | 80 | 20 | 100 | 90 | 0 | 20 | 40 |
| 77 | 2000 | 70 | 60 | 90 | 100 | 50 | 0 | 20 | 0 |
| 78 | 2000 | 0 | 0 | 0 | 20 | 70 | 0 | 0 | 0 |

EXAMPLE 31

Evaluation of Pre-Emergence Herbicidal Activity

Representative compounds of Formula I were evaluated for the pre-emergence control of a variety of species of plants. In these evaluations, seeds were planted in pots in an agricultural soil and immediately thereafter measured quantities of the test chemical were drenched onto the soil surface as an aqueous emulsion or suspension and allowed to leach into the soil. The aqueous emulsions or suspensions were prepared by mixing the required amount of active ingredient in an aqueous acetone carrier containing 0.1 percent by weight surface-active agent. Control pots were drenched with a like mixture omitting the active ingredient. The pots were maintained in a green house under conditions conducive to germination and growth. About 2 weeks after treatment the test was graded on a scale of 0–100 where 0 represents no effect and 100 represents complete kill. The plant species and compounds tested, the application rates employed, and the results obtained in this test are given in Table IV.

TABLE IV

PRE-EMERGENCE HERBICIDAL ACTIVITY

| Compound Number | Rate, lb/A | Yellow Nutsedge | Jimson-weed | Black Night-shade | Morning Glory | Pigweed | Velvet Leaf | Crab-grass | Yellow Foxtail | Corn | Rice | Wheat |
|---|---|---|---|---|---|---|---|---|---|---|---|---|
| 1 | 10.0 | — | — | 0 | 0 | 0 | 0 | 100 | 70 | — | — | — |
| 2 | 4.0 | 75 | 95 | — | — | — | 95 | — | 100 | 95 | 95 | 20 |
|   | 0.5 | 0 | 95 | — | 0 | — | — | — | 85 | 25 | 0 | 0 |
| 3 | 4.0 | 100 | 100 | — | 60 | — | 100 | — | 80 | 90 | 80 | 0 |
|   | 0.5 | 45 | 50 | — | 0 | — | 90 | — | 55 | 30 | 0 | 0 |
| 5 | 10.0 | — | — | 100 | 100 | 100 | 100 | 100 | 100 | — | — | — |
| 6 | 4.0 | 20 | — | — | 95 | — | 90 | — | 0 | 0 | 0 | 0 |
| 7 | 10.0 | — | — | 100 | 100 | 100 | 100 | 100 | 100 | — | — | — |
| 45 | 10.0 | — | — | 100 | 100 | 100 | 50 | 90 | 80 | — | — | — |
| 57 | 10.0 | — | — | 100 | — | 100 | 90 | 90 | 90 | — | — | — |
| 58 | 10.0 | — | — | 100 | 0 | 100 | 0 | 100 | 60 | — | — | — |
| 59 | 10.0 | — | — | 100 | — | 100 | 90 | 90 | 80 | — | — | — |
| 60 | 10.0 | — | — | 80 | 0 | 80 | 40 | 40 | — | — | — | — |
| 72 | 10.0 | — | — | 20 | 10 | 60 | 40 | 0 | 40 | — | — | — |
| 76 | 10.0 | — | — | 100 | 20 | 100 | 90 | 80 | 80 | — | — | — |
| 77 | 10.0 | — | — | 100 | 90 | 100 | 90 | 0 | 0 | — | — | — |
| 78 | 10.0 | — | — | 100 | 20 | 100 | 90 | 90 | 90 | — | — | — |

What is claimed is:

1. An imidazolo[1,2-a]pyrimidine-2-sulfonyl halide compound of the formula

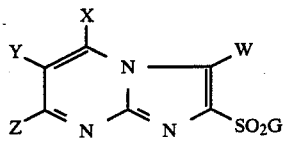

wherein
X and Z each, independently represents R, $OR^3$, $SR^3$, $NR^1R^2$, F, Cl, Br, or CN;
Y represents R, $OR^3$, F, Cl, Br, or CN;
W represents R, OR, $SO_nR^3$, $NR^1R^2$, F, Cl, Br, $NO_2$, CN, C(O)E, or phenyl, phenoxy, or phenylthio, each phenyl optionally having 1 to 3 substituents selected from the group consisting of F, Cl, Br, CN, $CF_3$, $NO_2$, and $CH_3$;
G represents Cl or Br;
R represents H, $C_1$-$C_4$ alkyl or $C_1$-$C_4$ haloalkyl;
$R^1$ and $R^2$ each, independently represents H or $C_1$-$C_4$ alkyl;
$R^3$ represents $C_1$-$C_4$ alkyl or $C_1$-$C_4$ haloalkyl;
E represents R, OR, SR, $NR^1R^2$, or phenyl; and
n represents an integer of 0, 1, or 2.

2. A compound according to claim 1 wherein G represents Cl.

3. A compound according to claim 64 wherein X and Z each, independently represents H, F, Cl, Br, $C_1$-$C_4$ alkyl, $C_1$-$C_4$ haloalkyl, $C_1$-$C_4$ alkoxy, or $C_1$-$C_4$ alkylthio.

4. A compound according to claim 1 wherein Y represents H, chloro, or $C_1$-$C_4$ alkyl.

5. A compound according to claim 1 wherein W represents R, F, Cl, Br, $NO_2$, CN, C(O) $C_1$-$C_4$ alkyl, or $CO_2$ $C_1$-$C_4$ alkyl.

6. A compound according to claim 1 wherein X and Z each, independently represents H, F, Cl, Br, $C_1$-$C_4$ alkyl, $C_1$-$C_4$ haloalkyl, $C_1$-$C_4$ alkoxy, or $C_1$-$C_4$ alkylthio; Y represents H, chloro, or $C_1$-$C_4$ alkyl; W represents R, F, Cl, Br, $NO_2$, CN, C(O) $C_1$-$C_4$ alkyl, or $CO_2$ $C_1$-$C_4$ alkyl; and G represents Cl.

7. A compound according to claim 6 wherein X and Z each represents $CH_3$; Y represents H; W represents H, Cl, or Br; and G represents Cl.

8. An imidazolo[1,2-a]pyrimidine-2-sulfonic acid compound of the formula

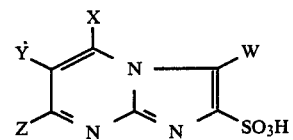

wherein
X and Z each, independently represents R, $OR^3$, $SR^3$, $NR^1R^2$, F, Cl, Br, or CN;
Y represents R, $OR^3$, F, Cl, Br, or CN;
W represents R, OR, $SO_nR^3$, $NR^1R^2$, F, Cl, Br, $NO_2$, CN, C(O)E, or phenyl, phenoxy, or phenylthio, each phenyl optionally having 1 to 3 substituents selected from the group consisting of F, Cl, Br, CN, $CF_3$, $NO_2$, and $CH_3$;
R represents H, $C_1$-$C_4$ alkyl, or $C_1$-$C_4$ haloalkyl;
$R^1$ and $R^2$ each, independently represents H or $C_1$-$C_4$ alkyl;
$R^3$ represents $C_1$-$C_4$ alkyl or $C_1$-$C_4$ haloalkyl;
E represents R, OR, SR, $NR^1R^2$, or phenyl;
n represents an integer of 0, 1, or 2; and
alkali metal and amine salts thereof.

9. A compound according to claim 8 wherein X and Z each, independently represents H, F, Cl, Br, $C_1$-$C_4$ alkyl, $C_1$-$C_4$ haloalkyl, $C_1$-$C_4$ alkoxy, or $C_1$-$C_4$ alkylthio.

10. A compound according to claim 8 wherein Y represents H, chloro, or $C_1$-$C_4$ alkyl.

11. A compound according to claim 8 wherein W represents R, F, Cl, Br, $NO_2$, CN, C(O) $C_1$-$C_4$ alkyl, or $CO_2$ $C_1$-$C_4$ alkyl.

12. A compound according to claim 8 wherein X and Z each, independently represents H, F, Cl, Br, $C_1$-$C_4$ alkyl, $C_1$-$C_4$ haloalkyl, $C_1$-$C_4$ alkoxy, or $C_1$-$C_4$ alkylthio; Y represents H, chloro, or $C_1$-$C_4$ alkyl; and W represents R, F, Cl, Br, $NO_2$, CN, C(O) $C_1$-$C_4$ alkyl, or $CO_2$ $C_1$-$C_4$ alkyl.

13. A compound according to claim 12 wherein X and Z each represents $CH_3$; Y represents H; and W represents H, Cl, or Br.

* * * * *

UNITED STATES PATENT AND TRADEMARK OFFICE
CERTIFICATE OF CORRECTION

PATENT NO. : 4,731,446
DATED : March 15, 1988
INVENTOR(S) : N. R. Pearson et al.

It is certified that error appears in the above-identified patent and that said Letters Patent is hereby corrected as shown below:

Col. 20, line 66, delete "$C_{15}H_{14}C_{12}N_4O_2S$" and insert -- $C_{15}H_{14}Cl_2N_4O_2S$ --;

Col. 24, line 60, delete second reference to "was";

Col. 24, line 61, delete "as" and insert -- was --;

Col. 33, line 54, delete "claim 64" and insert -- claim 1 --;

Signed and Sealed this

Twenty-sixth Day of May, 1992

Attest:

DOUGLAS B. COMER

Attesting Officer

Acting Commissioner of Patents and Trademarks